United States Patent [19]

Olson

[11] Patent Number: 5,001,072

[45] Date of Patent: * Mar. 19, 1991

[54] COMPOSITIONS AND METHODS FOR MULTIPLE SIMULTANEOUS IMMUNORADIOMETRIC ASSAY (IRMA) OF ANALYTES USING RADIOISOTOPE CHELATE LABELS

[75] Inventor: Douglas R. Olson, Doylestown, Pa.

[73] Assignee: ICN Biomedicals Inc., Costa Mesa, Calif.

[ * ] Notice: The portion of the term of this patent subsequent to Jun. 9, 2004 has been disclaimed.

[21] Appl. No.: 59,017

[22] Filed: Jun. 8, 1987

Related U.S. Application Data

[63] Continuation-in-part of Ser. No. 612,979, May 23, 1984, Pat. No. 4,672,028.

[51] Int. Cl.$^5$ ............................................. G01N 33/534
[52] U.S. Cl. ..................... 436/500; 436/505; 436/538; 436/539; 436/540; 436/542; 436/545; 436/548; 436/804; 530/389; 530/402
[58] Field of Search ............... 436/500, 501, 504, 505, 436/538, 539, 540, 542, 545, 548, 804, 815, 817; 530/389, 402

[56] References Cited

U.S. PATENT DOCUMENTS

| | | | |
|---|---|---|---|
| 4,352,751 | 10/1982 | Wieder et al. | 436/71 |
| 4,460,561 | 7/1984 | Goldenberg | 530/389 |
| 4,472,509 | 9/1984 | Gansow et al. | 436/804 |
| 4,652,519 | 3/1987 | Warshawsky et al. | 436/815 |
| 4,741,900 | 5/1988 | Alvarez et al. | 530/389 |
| 4,767,609 | 8/1988 | Stavrianpoulos | 530/402 |

OTHER PUBLICATIONS

Meares et al., "Covalent Attachment of Metal Chelates to Proteins: The Stability in Vivo and in Vitro of the Conjugate of Albumin with a Chelate of $^{111}$Indium"; Proc. Natl. Acad. Sci., U.S.A., 73(11), 1976, 3803–3806.

Primary Examiner—Christine Nucker
Attorney, Agent, or Firm—Lyon & Lyon

[57] ABSTRACT

Compositions and methods are disclosed for multiple simultaneous assays of different analytes using radioactive labeled antibodies to the analytes, at least one portion of the assay being an immunoradiometric assay in which there is employed a metal isotope label, e.g., $^{57}$Co, attached to an antibody to the analyte through a chelator, e.g., ethylenediaminetetraacetic acid. Multiple simultaneous immunoradiometric assays can be performed by this method, as can multiple simultaneous assays in which one portion of the assay is an immunoradiometric assay and another portion or portions involve one or more other radioassay techniques.

22 Claims, No Drawings

COMPOSITIONS AND METHODS FOR MULTIPLE SIMULTANEOUS IMMUNORADIOMETRIC ASSAY (IRMA) OF ANALYTES USING RADIOISOTOPE CHELATE LABELS

This application is a continuation-in-part of copending U.S. patent application Ser. No. 612,979, filed May 23, 1984, now U.S. Pat. No. 4,671,028, entitled "Composition and Methods for Simultaneous Multiple Assay of Analytes Using Radioisotope Chelate Labels."

FIELD OF THE INVENTION

Radioimmunoassay is an analytical technique that resulted from the work of Berson and Yalow. In radioimmunoassay, radiolabeled exogenous antigen competes with unlabeled endogenous antigen for binding sites on an antibody or specific binding proteins, e.g. intrinsic factor, made specifically to the antigen.

The percentage of bound radiolabeled antigen decreases as a function of the increasing concentration of unlabeled antigen in the test sample. Separation of the bound and free radiolabeled antigen is necessary in order to determine the quantity of unlabeled antigen. This can be accomplished by insolubilization of the antigen-antibody complexes either by chemical means, e.g., polyethylene glycol precipitation, or by the addition of a second antibody directed toward the immunoglobulin present in the original antiserum, or by a combination of these two methods. The quantity of unlabeled antigen in an unknown sample is then determined by comparing the radioactivity of the precipitate, after centrifugation, with values established using known standards in the same assay system.

Assays using radiolabeled antibodies to analytes, with which this invention is particularly concerned, are known as immunoradiometric assays (IRMAs).

This invention relates to a method by which two or more analytes may be measured simultaneously in the same tube wherein an antibody to the material to be assayed is radiolabeled. The invention also relates to the preparation of the labeled antibodies to such analytes employing chelating agents.

BACKGROUND OF THE INVENTION

There is a continuing search for cheaper and quicker analytical procedures. One way to accomplish this is to have an assay whereby two or more analytes can be assayed simultaneously in the same solution.

An example is in U.S. Pat. No. 4,146,602, issued on Mar. 27, 1979, which discloses a simultaneous assay of folate and Vitamin $B_{12}$. $^{57}$Co is incorporated in Vitamin $B_{12}$ which is rather uncomplicated since Vitamin $B_{12}$ is a cobalt containing compound. The problem was how to incorporate $^{57}$Co into noncobalt containing analytes.

The use of chelating agents is well known; however, there is no known use of chelating agents to prepare analytes useful in simultaneous assays.

A paper by Yeh et al., *J. Radioanal. Chem.*, 53, (1979) 327–336 describes the preparation of an assay of indium chelates. A chapter in the American Chemical Society publication *Advances In Chemistry Series. No. 198, Modification of Proteins*, 369–387, by Meares et al. discusses chelate tagged proteins and polypeptides using cobalt to prepare radiopharmaceuticals.

Egan et al., "$^{57}$Co: A Volume Mark for the TRIPLE-ISOTOPE, Double-Antibody Radioimmune Assay", *Immunochemistry*. 14 (1977) 611–613 discuss using a chelating agent (ethylenediaminetetraacetic acid) with cobalt, but to prevent adsorption of cobalt to serum proteins.

SUMMARY OF THE INVENTION

The invention disclosed in copending U.S. patent application Ser. No. 612,979 embodies the discovery that by employing chelating agents it is possible to label different analytes, or antibodies thereto, with different radionuclides to provide a method for more efficient and quicker assays on multiple analytes in a single tube, simultaneously. Radionuclides are introduced into analytes or antibodies thereto by way of analyte-bound or analyte antibody-bound chelating moieties, and the thus-obtained radiolabeled analytes or antibodies thereto are used in radioassays for said analytes. These radiolabeled analytes or antibodies thereto containing individually distinguishable radionuclides may be combined in a variety of configurations such that one or more analytes may be measured simultaneously by immunoradiometric assay (IRMA). As taught in this copending application analytes or antibodies thereto labeled in this manner could also be combined with analytes or antibodies thereto labeled by alternate means to provide multiple simultaneous assays, one portion of which is an immunoradiometric assay.

This disclosed assay method thus comprises employing a coordination compound of the general formula:

metal isotope—chelator—organic species (analyte or antibody thereto)

Copending application Ser. No. 612,979, the disclosure of which is incorporated herein in its entirety by reference, makes specific reference to metal isotope labeling of purified antibodies to different analytes to construct an immunoradiometric assay. The present application amplifies this disclosure.

More particularly, this invention provides compositions and methods for multiple simultaneous assays of different analytes using radioactive labeled antibodies to the analytes, at least one portion of the assay being an immunoradiometric assay (IRMA) in which there is employed a metal isotope label, e.g., $^{57}$Co, attached to an antibody to the analyte through a chelator, e.g., ethylenediaminetetraacetic acid. Multiple simultaneous immunoradiometric assays can be performed by this method, as can multiple simultaneous assays in which one portion of the assay is an immunoradiometric assay and another portion or portions involve one or more other radioassay techniques, e.g., a competitive radioimmunoassay (RIA).

It is therefore an object of this invention to provide compositions and methods for multiple simultaneous immunoradiometric assay (IRMA) of different analytes.

It is also an object of this invention to provide compositions and methods for multiple simultaneous immunoradiometric assay of different analytes using radioactive labeled antibodies to different analytes, said antibodies having been purified, if necessary, using art-recognized techniques, in which different radioactive labels are attached to the antibodies through chelating agents.

A further object of this invention is to provide compositions and methods for a dual simultaneous radioimmunoassay (RIA)/immunoradiometric assay (IRMA)

in which a radioactive metal-chelator-antibody to analyte product is used in the IRMA half of the assay.

These and other objects, as well as the nature, scope and utilization of this invention, will become readily apparent to those skilled in the art from the following description and the appended claims.

ANALYTES

Included among the analytes which can be determined by means of the multiple simultaneous assay methods of this invention are any organic species which can react with (bind to) an antibody therefor. In general, they include steroids such as estrogens, progesterone, digoxin, cortisol, 17-hydroxyprogesterone and the like; proteins, such as human chorionic gonadotropin, luteinizing hormone, follicle stimulating hormone, thyroid stimulating hormone, α-fetoprotein, trypsin, hepatitis associated antigen, carcinoembryonic antigen and the like; peptides, such as ACTH, endorphins, angiotensin, insulin and the like; carbohydrates, such as pneumococal polysaccharides and the like; drugs, such as cocaine, tetrahydrocannibinol, barbiturates, amphetamines and the like; antibiotics, such as gentamicin, and the like.

Specific pairs of analytes which could be analyzed simultaneously include the following:

1. Carcinoembryonic antigen (CEA) β-hCG, α-fetoprotein, or any other two tumor markers;
2. LH/FSH;
3. Hepatitis B surface antigen/hepatitis B core antigen or any other two viral antigens;
4. Thyroxine/thyroid stimulating hormone (TSH) in screening for neonatal hypothyroidism;
5. Thyroxine/thyroid binding globulin (for T3U) in diagnosis and treatment of adult thyroid disease;
6. Angiotension II/renin in diagnosing the cause of hypertension;
7. Adrenocorticotrophic hormone (ACTH)/cortisol in differentiating primary from secondary adrenal disease;
8. Insulin/C-peptide in the diagnosis and treatment of diabetes;
9. Estriol/human placentral lactogen in monitoring pregnancy;
10. Lactate dehydrogenase (LDH)/creatine phosphokinase (CPK) isoenzymes in diagnosing heart disease;
11. Serological screening of donor blood for any two viruses or venereal infections simultaneously, such as hepatitis-B surface antigen and human T-cell leukemia virus antigens or antibodies to same; and
12. TSH/ferritin in a dual assay in which a two site IRMA is carried out to measure TSH and a competitive assay for ferritin, e.g., one using exogeneous $^{125}I$ labeled ferritin, is carried out simultaneously.

CHELATING AGENTS

The holding of a metal ion between two or more atoms of a single molecule is called chelation. There are many naturally occurring compounds which are chelates, including hemoglobin, Vitamin $B_{12}$, chlorophyll and siderophores. In addition, there are numerous other compounds that are capable of forming chelates: β-diketones, polyaminepolycarboxylic acids or polycarboxylates, quinolinols and naphthols are among those which form relatively strong complexes with metals.

Chelating agents best suited for use in practicing this invention have the following characteristics:

1. They must be water soluble.
2. They must form strong chelates with radioactive metals, e.g., $^{57}Co$ in solution,
3. They must be capable of easily forming stable covalent linkages with the antibodies of interest, and once attached to an antibody to an analyte they must retain their ability to form coordination complexes with +2 and +3 metal radionuclides.
4. The formed complexes of antibody to an analyte, chelator and metal radionuclide must retain all or at least part of the binding specificity of the native analyte antibody.
5. They must be easily and inexpensively obtainable in relatively pure form.

Among the chelating agents from which the chelator portion of the coordination compounds of this invention can be derived are polyaminopolycarboxylates of the following general formula:

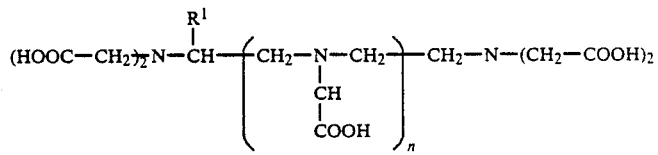

wherein $R^1$ is hydrogen, phenyl or substituted phenyl, with the substituents being, e.g., $NO_2$, $NH_2$, $SO_2H$ and the like, and n is an integer of 0 or 1. Included among such polyaminopolycarboxylates are ethylenediaminetetraacetic acid (EDTA), ethylenedinitrilotetraacetic acid, diethylenetriaminepentaacetic acid (DTPA), and derivatives thereof, such as 1-(p-bromoacetamidobenzyl)ethylenediaminetetraacetic acid, hydroxyethylethylenediaminetetraacetic acid (HEDTA), and the like.

Naturally occurring chelates such as Vitamin $B_{12}$ can also be used.

RADIONUCLIDES

The choice of any particular radionuclide to be used for labeling is governed by the following practical considerations:

1. It preferably should be one which has a half life of a reasonable period of time, i.e., a half life sufficiently long to enable it to be used over a practical period of time, such as several weeks or months. It should be understood, however, that isotopes of even relatively short half life can be used in practicing this invention.
2. It must be available in sufficiently high specific activity to provide an adequate signal amplification.
3. It must possess a relatively unique emission spectrum when used in combination with one or more other radionuclides.

In general, any radioisotope of a metal can be employed. Preferred isotopes include those of the metals cobalt, iron, indium, technetium, europium and terbium. Especially preferred are isotopes of cobalt and iron, with cobalt 57 ($^{57}Co$) and iron 59 ($^{59}Fe$) being most preferred.

PREPARATION OF LABELED ANTIBODIES TO ANALYTES

The labeled antibodies to the analytes being determined are prepared by first reacting the chelating agent with purified antibody to the analyte at a temperature in the range of from about 4° C. to about 40° C. in a basic solution of a solvent, such as 0.1 M sodium bicarbonate.

The reaction mixture is then purified by passing it through a molecular sieve, such as Sephadex G75 or a comparable polyacrylamide or other polymeric molecular sieve.

The thus-purified antibody-chelator product is reacted with the labeling metal isotope at a temperature in the range of from about 4° C. to about 40° C. in the presence of a substantially metal-free buffer, e.g., one containing as small an amount of metals such as sodium (from sodium acetate), potassium (from potassium acetate), or the like, as can readily be achieved in commercial practice.

To obtain the best products and the greatest gains in specific activity, the product itself should be substantially free of metal contaminants, i.e., as many sources of metal contamination as possible should be eliminated, since presumably any metal contaminants present will compete with the radionuclide for attachment sites on the chelating agent. Metals can be removed from antibody or other protein solutions, water and buffers by treatment with appropriate ion exchange resins, e.g., Chelex ion exchange resin (available from Bio-Rad). Plastic reaction vessels, pipettes, etc. should be used where possible, and should in general be acid washed to remove metal contaminants.

The long-term stability of the metal isotope labeled antibody-chelator product, i.e., the ability of the radionuclide to remain specifically attached to the chelator over a period of weeks or months, can be affected by a number of factors. For example:

1. Lyophilization of the radionuclide labeled antibody-chelator product, if carried out in such a manner as to limit moisture contamination and melt-back, can stabilize this material for long periods of time.

2. Stability is "concentration dependent" in solution. In other words, highly concentrated radionuclide labeled antibody-chelator solutions may exhibit significantly greater stability than more dilute solutions of the same products. This may be because when solutions of these labeled products are diluted, the relative concentrations of radionuclide to metal contaminants change dramatically. At this point the relatively higher concentrations of metal contaminants can displace the radionuclide from the chelator.

3. Many metals, including cobalt, can form insoluble complexes with anions, such as the phosphate ion, found in abundance in most biological preparations. When a radionuclide becomes separated from the chelator, it is often observed to be present in the bound phase of a double antibody/PEG RIA in the absence of primary antibody, i.e., non-specific binding occurs. Presumably, this is due to the radionuclide's forming insoluble complexes with anions present and then being removed from the "free" solution phase, e.g., by centrifugation.

4. The stability of radionuclide labeled antibody-chelator products in solution can be improved by introducing additional chelator, such as EDTA, into the system,. There appears to be an optimum empirically determinable concentration of chelator for each system, i.e., solutions having chelator concentrations above and below the optimum concentration exhibit greater instability than do those at the optimum concentration. A hypothesis by which this behavior can be explained is this: Chelators such as EDTA are quite effective in complexing metal contaminants, even when the chelator is present in very low concentrations, and thus limit the ability of such contaminants to displace the radionuclide from the chelator bound to the antibody. Increasing the amount of chelator present will improve stability up to the point at which all the competing metal contaminant has been complexed. At this point, the addition of further chelator will lead to some loss of stability, since the added chelator can then compete with the antibody-bound chelator for radionuclide.

Monoclonal and polyclonal antibodies to analytes may be labeled in accordance with the method of this invention for use in multiple simultaneous immunoradiometric assays. Such antibodies are prepared by techniques which are so well known in the art that they need not be described herein any great detail.

Monoclonal antibodies useful in practicing this invention can be produced, for example, by monoclonal hybrid cells or hybridomas obtained by fusing myeloma cells with antibody-producing cells using the techniques described initially by Kohler and Milstein in *Nature*, 256, 495–497 (1975) and *Eur. J Immunol.*, 6, 511–519 (1976). These techniques were later expanded upon by Milstein et al., *Nature*, 266, 550–552 (1977); Walsh, *Nature*, 266, 495 (1977); Gefter et al., *Somatic Cell Genet.*, 3, 231–236 (1977); Barnstable et al., *Cell*, 14, 9–20 (1978); Parham et al., *Nature*, 276 397–399 (1978); Melchers et al., Eds., "Current Topics in Microbiology and Immunology", Vol. 81—"Lymphocyte Hybridomas" (Berlin: Springer-Verlag, 1978), and see the references contained therein; Weir, Ed., "Handbook of Experimental Immunology", Third edition, Vol. 2, Chap. 25 (London:Blackwell, 1978), and see the references contained therein; Koprowski et al, *Proc. Natn'l. Acad. Sci. USA*. 75, 3405–3409 (1978); Fox, *C&EN*. Jan. 1, 1979, 15–17; in U.S. Pat. Nos. 4,172,124; 4,271,145; 4,322,274; 4,331,647; 4,349,528; 4,350,683; 4,361,549; 4,361,550; 4,363,799 and 4,364,932–'937, in U.K. Patent Application Nos. 2,039,948A and 2,079,313A, and in European Patent Application No. 0,014,519.

In order that those skilled in the art can more fully understand this invention, the following examples are set forth. These examples are given solely for purposes of illustration, and should not be considered as expressing limitations unless so set forth in the appended claims. All parts and percentages are by weight, unless otherwise stated.

EXAMPLE I

This example illustrates the use of this invention in an immunoradiometric assay for thyroxine and thyroid stimulating hormone (TSH).

A three gram sample of thyroxine sodium salt was partly dissolved in 30 ml of ethanol. After addition of 30 ml of 2 N ammonium hydroxide, the mixture was gravity filtered into 60 ml of cold 5% hydrochloric acid. The white precipitate was then collected by suction filtration, washed with water and dried under vacuum. 1.5 Grams of product resulted. This product was dissolved in 35 ml of dimethylformamide in a 250 ml flask, to which 25 ml of acetic anhydride were added. The resulting mixture was stirred at room temperature (about 18°–22° C.) for 2.5 hours, and water was added until the solution became cloudy. The solution was then cooled at 4° C. overnight. The product was filtered, washed with water and redissolved in ethanol. The solution was then treated with 13 ml of 1M sodium hydroxide for 1 hour. The product was precipitated with cold 5% hydrochloric acid, filtered and dried in vacuum. This resulted in 1.1 grams of N-acetyl thyroxine.

1.0 Gram of N-acetyl thyroxine was dissolved in a mixture of 2 ml of dimethylformamide and 2 ml of tetrahydrofuran. 0.155 Gram of N-hydroxysuccinimide was added to the solution, followed by 0.268 gram of N,N'-dicyclohexylcarbodiimide. The mixture was stirred for 6 hours, filtered, the tetrahydrofuran evaporated, and the dimethylformamide removed under vacuum. The resulting sticky solid was redissolved with a diethylether/hexanes mixture and then dried to a yellow solid. This resulted in 1.14 grams of the N-hydroxysuccinimide ester of N-acetyl thyroxine.

Freshly distilled 1,6-hexanediamine was dissolved in ethanol. To this solution, 1.1 equivalents of triethylamine and $\frac{1}{3}$ equivalent of ethyltrifluoroacetate were added, and the resulting mixture was stirred at room temperature overnight. The ethanol was removed on a rotary evaporator and the residue was fractionally distilled under reduced pressure (water aspirator). The first fraction (b.p. 89°–91° C.) was starting material. The residue, protected diamine, crystallized slowly upon standing.

100 Milligrams of the N-hydroxysuccinimide ester of N-acetyl thyroxine were dissolved in dimethylformamide and 58 milligrams of the protected diamine added. After 5 minutes, a precipitate formed and was allowed to stir overnight. Product formation was monitored by thin layer chromatography (TLC); trichloromethane:ethanol 10:1. When all of the starting material had reacted (as shown by TLC), the dimethylformamide was evaporated and the yellow residue redissolved in ethanol. The product was precipitated by dropwise addition of water and collected by centrifugation. The solid was then absorbed on silica gel by dissolving in dimethylformamide. The absorbed product was then placed on a silica gel column and eluted with trichloromethane:ethanol (10:1). Ninhydrin was used on TLC to demonstrate removal of the protective group of the amine.

The resulting $T_4$-bridge compound was dissolved in dimethylformamide/dimethylsulfoxide (1:1) and 10 equivalents of diethylenetriaminepentaacetic anhydride (DTPA) added. The solution was stirred at room temperature, and the solvents then evaporated. The residue was purified on Sephadex G-25 (1×20 cm) using water followed by 0.1 N sodium hydroxide to elute the product. A 2% yield of $T_4$-bridge-DTPA product was obtained.

1 Ml of this product was acidified (<pH 3.0) with 2 N hydrochloric acid (0.05 ml). A Sephadex G-25 column (1×15 cm) was washed with 75 ml of water which had been passed through a chelex ion exchange resin to remove metals. All subsequent steps were performed to limit exposure to metals. The acidified product was added to the column and washed with 2 ml of 0.1 N hydrochloric acid. This initial eluant was collected and added back to the column. The column was washed with an additional 10 ml of 0.1 N hydrochloric acid. The contents of the column were poured into a plastic centrifuge tube, rinsing with small volumes of 0.1 N hydrochloric acid. To this slurry, 20 μl of $^{57}Co$ (2 mCi) were added along with 10 ml of 0.5 M acetate buffer (pH 5.6) and vortexed. The reaction mixture was incubated for 2.5 hours at room temperature with gentle rotation. The slurry was then repoured into a column (1×20 cm) and allowed to settle. The initial eluant and eluant collected during a 5 ml water wash were discarded. The column was then eluted with 20 ml of 0.1 N sodium hydroxide and 10 ml of water. This eluant contained the $^{57}Co$ labeled $T_4$-bridge-DTPA product.

PREPARATION OF $^{125}I$ LABELED RABBIT ANTI-TSH

600 Microliters of purified rabbit anti-TSH at a concentration of 1 mg/ml in pH 8.0 tris-sodium chloride buffer was added with 700 μl of 0.1 M phosphate buffer (pH 7.5) to a 3 ml silanized reaction vial. 600 Microliters of 0.4 M phosphate buffer (pH 7.5) containing 20 mCi of $^{125}I$ was added to the vial. Reaction was initiated by adding 25 μl of a 10 mg/ml solution of chloramine-T (0.1 M phosphate buffer, pH 7.5) and mixing. The reaction was terminated after 60 seconds by adding to the reaction mixture 50 μl of sodium metabisulfite (10 mg/ml in 0.1 M phosphate buffer, pH 7.5) and vortexing.

Immediately after termination of the reaction, the reaction mixture was transferred to a Sephadex G-75 column (0.5×26.0 cm), equilibrated and eluted with 0.1% bovine serum albumin in phosphate buffered saline, pH 7.5. 0.5 Milliliter fractions were collected. The $^{125}I$ labeled rabbit anti-TSH eluted between fractions 12–18. All fractions which were on the ascending side of the peak which contained greater than 33% of the activity of the peak tube or were on the descending side of the peak which contained greater than 50% of the activity of the peak tube were pooled. The pooled fractions were diluted in 3% bovine serum albumin in phosphate buffered saline, pH 7.5, to a concentration of 10 μCi/ml and stored at 4° C.

ASSAY BACKGROUND

The principle of the thyrotropin or TSH measurement in the dual test is based on a two site immunoradiometric assay (IRMA). The system utilized monoclonal antibody treated cellulose particles and a radiolabeled purified antibody. The sample and radiolabeled (125I) antibody were incubated with antibody treated cellulose in a tube. During the incubation, the radiolabeled antibody reacted with the bound TSH. The tube was then centrifuged and decanted to remove the free or unbound labeled antibody. The radioactivity bound to the antigen on the solid phase ("bound counts") was measured in a gamma counter. The bound counts in the sample assay tube were compared with values obtained from known TSH concentration standards. The TSH concentration in the patient sample could then be calculated.

The principle of the thyroxine or $T_4$ measurement in the dual test is based on a competitive radioimmunoassay (RIA). In this assay, radiolabeled ($^{57}Co$) $T_4$ competed with unlabeled endogenous $T_4$ for binding sites on the immobilized $T_4$ antibody. After the incubation period was completed, the $T_4$ antibody complex was separated from free $T_4$ by centrifugation and decanting of the assay tubes. The amount of radiolabeled $T_4$ bound to the antibody in the assay was compared to values obtained from known $T_4$ concentration standards. The $T_4$ concentration in the patient sample could then be calculated.

REAGENTS

TSH/T$_4$ Cellulose

Purified mouse monoclonal anti-TSH and rabbit anti-T$_4$ antibodies immobilized on microcrystalline cellulose in phosphate buffer with protein stabilizers and 0.1% sodium azide as a preservative. Stored at 4° C.

TSH $^{125}$I Tracer Solution $^{125}$I Labeled rabbit anti-TSH in phosphate buffered saline with a protein stabilizer and 0.1% sodium azide as a 10 μCi/11 ml. Stored at 4° C.

T$_4$ $^{57}$Co Tracer Solution $^{57}$Co labeled T$_4$ diluted to 100,000 cpm/10 μl in ANS/sodium barbital solution at pH 8.6 with 0.1% sodium azide as a preservative. Stored at 4° C.

TSH/T$_4$ Standard

Seven vials each containing TSH/T$_4$ in porcine serum with preservatives. Concentrations of the standards were as follows:
0/0, 0.5/1, 1/2.5, 2/5 10/10, 25/15 and 100/25 82 IU of TSH per ml/μg of T$_4$ per dl.

ASSAY PROCEDURE 1. 12×75 Assay tubes were labeled according to the following general outline:

| Assay Tube | Contents | |
|---|---|---|
| 1, 2 | Standard: | 0.0 μIU/ml TSH; 0.0 μg/dl T$_4$ |
| 3, 4 | | 0.5 μIU/ml TSH; 1.0 μg/dl T$_4$ |
| 5, 6 | | 1.0 μIU/ml TSH; 2.5 μg/dl T$_4$ |
| 7, 8 | | 2.0 μIU/ml TSH; 5.0 μg/dl T$_4$ |
| 9, 10 | | 10.0. μIU/ml TSH; 10.0 μg/dl T$_4$ |
| 11, 12 | | 25.0 μIU/ml TSH; 15.0 μg/dl T$_4$ |
| 13, 14 | | 100.0 μIU/ml TSH; 25.0 μg/dl T$_4$ |
| 15, 16 | Control Sample CI | |
| 17, 18 | control Sample CII | |
| 19–100 | Patient Samples | |

2. 100 Microliter portions of standards, controls, and serum samples were accurately pipetted into appropriately labeled tubes.

3. 100 Microliter portions of TSH/T$_4$ cellulose solution were accurately pipetted into all of the assay tubes.

4. A 100 μl portion of TSH tracer solution and 100 μl of T$_4$ tracer solution were accurately pipetted into each assay tube.

5. Incubation took place at room temperature (18°–22° C.) for 3 hours on a laboratory shaker.

6. Five milliliter portions of distilled water were added to each assay tube, and each tube was centrifuged 10 minutes at 3000 cpm and decanted. The pellet was resuspended in 5 ml distilled water, centrifuged, and decanted. The tubes were counted on a gamma counter set respectively for $^{125}$I and $^{57}$Co for TSH and T$_4$.

CALCULATION OF RESULTS

1. The counts per minute (cpm) were averaged for all duplicate tubes. Correction for background was made.
2. The mean cpm's for each standard were plotted on semilogarithmic graph paper using the abscissa (logarithmic scale) for the concentration of the standard. A smooth curve was drawn through all points.
3. Unknown samples were interpolated with the standard curve.

TYPICAL DATA

| Tube Contents | TSH($^{125}$I) Average CPM | T$_4$ ($_{57}$CO) Average CPM |
|---|---|---|
| 0/0 Standard | 787 | 6417 |
| 0.5/1 Standard | 875 | 4717 |
| 1/2.5 Standard | 964 | 3422 |
| 2/5 Standard | 1211 | 2386 |
| 10/10 Standard | 2590 | 1702 |
| 25/15 Standard | 5537 | 1332 |
| 100/25 Standard | 15817 | 966 |

PERFORMANCE CHARACTERISTICS

Results of Intra- and Inter-Assay Variation

| | Pool 1 | | Pool 2 | |
|---|---|---|---|---|
| | Intra-Assay | Inter-Assay | Intra-Assay | Inter-Assay |
| TSH | | | | |
| x (μIU/ml) | 4.64 | 4.64 | 18.73 | 18.73 |
| s (μIU/ml) | 0.36 | 0.15 | 0.56 | 1.26 |
| CV (%) | 7.69 | 3.24 | 2.98 | 6.70 |
| n | 15 | 15 | 15 | 15 |
| m | 3 | 3 | 3 | 3 |
| T$_4$ | | | | |
| x (μg/dl) | 5.57 | 5.57 | 12.77 | 12.77 |
| s (μg/dl) | 0.28 | 0.25 | 0.80 | 0.88 |
| CV (%) | 4.94 | 4 45 | 6.29 | 6.93 |
| n | 5 | 15 | 15 | 15 |
| m | 3 | 3 | 3 | 3 |

Accuracy

A. Spike Recovery

T$_4$ and TSH were spiked into serum pools at three different levels. Recoveries were calculated from the average values.

| TSH Added (μIU/ml) | Average TSH Recovered (μIU/ml) | Average % Recovery |
|---|---|---|
| 6.5 | 5.6 | 117 |
| 13.0 | 11.0 | 98 |
| 26.0 | 21.0 | 99 |

| T$_4$ Added (μg/dl) | Average T$_4$ Recovered (μg/dl) | Average % Recovery |
|---|---|---|
| 5 | 5.6 | 112 |
| 10 | 11.0 | 110 |
| 20 | 21.0 | 105 |

B. Correlation With other Methods

A patient sample correlation was run against individual T$_4$ and TSH radioassays. A least squares linear regression analysis was then carried out on paired values obtained in the combination TSH/T$_4$.

Dual Assay procedure against the individual references assays. The results are summarized below.

| | n | slope | intercept | R | R$^2$ |
|---|---|---|---|---|---|
| TSH | 45 | 0.851 | −0.545 | 0.992 | 0.983 |
| T$_4$ | 45 | 1.062 | −1.535 | 0.962 | 0.926 |

EXAMPLE II

One milligram of lyophilized purified rabbit anti-TSH was mixed dry with 4.0 mg of diethylenetriaminepentaacetic anhydride (DTPA). 100 μl of metal-free 0.1 M HEPES was added and the reaction mixture vortexed. After thirty minutes at room temperature, the reaction mixture was passed through a Sephadex G-25 column, equilibrated and eluted with 0.5 M acetate buffer pH 5.8 (metal free). The anti-TSH-DTPA containing fractions were identified by absorbance at 280 nm. Peak fractions were pooled and diluted to 100 μg anti-TSH/ml with 0.5 M acetate buffer, pH 5.8.

100 Microliters of anti-TSH-DPTA (10 g) were added to 20 μl (1 mCi) of carrier-free 57 cobalt chloride in 0.5 N HCl and reacted for one and one half hours at room temperature. The reaction mixture was passed through a Sephadex G-75 column, equilibrated and eluted with phosphate buffered saline (PBS) containing 0.1% bovine serum albumin. The $^{57}$Co-DTPA-anti-TSH eluted near the void volume as a single peak. In general, 50% of the $^{57}$Co was chelated by the anti-TSH-DTPA precursor, yielding tracers with specific activities ranging from 10 to 15 μgCi/μg.

This material can be used in a single TSH IRMA assay, or to assay for TSH combined with other analytes.

EXAMPLE III

This example illustrates the use of this invention in dual RIA/IRMA assay for TSH/ferritin in which a radionuclide label-chelator-antibody product is used in the IRMA portion of the assay.

ASSAY BACKGROUND

The principle of thyrotropin (TSH) measurement in this dual assay is based on a two site immunoradiometric assay (IRMA). The system utilizes a purified rabbit anti-TSH antibody, along with a $^{57}$Co labeled purified goat anti-TSH antibody to form a "sandwich" in the presence of TSH from a sample or standard. This complex is removed from the unbound $^{57}$Co labeled goat anti-TSH by immunoprecipitation with goat anti-rabbit antiserum, followed by centrifugation and decantation. The amount of bound $^{57}$Co labeled goat anti-TSH in the pellet is determined using a gamma counter and is directly proportional to the amount of TSH in the sample. The bound counts in the sample assay tubes are compared with values obtained from known TSH concentration standards. The TSH concentration in an unknown sample can then be calculated.

The ferritin part of the dual assay is based on the principle of competitive binding between endogenous ferritin (analyte) and a small fixed amount of exogenous $^{125}$I labeled ferritin for sites on a fixed quantity of rabbit anti-ferritin antibody. The $^{125}$I ferritin-anti-ferritin complex is removed from the unbound ferritin tracer by immunoprecipitation with goat anti-rabbit antiserum. Upon certrifugation, a pellet containing the bound complex is formed and the unbound tracer is removed by decantation. The amount of bound tracer in the pellet is measured using a gamma counter and is inversely proportional to the amount of ferritin present in the sample. The bound counts in the sample assay tubes are compared with values obtained from known ferritin concentration standards. The ferritin concentration in an unknown sample can then be calculated.

REAGENTS

$^{125}$I Ferritin/$^{57}$Co Anti-TSH Tracer $^{125}$I labeled ferritin and $^{57}$Co labeled goat anti-TSH antibody were prepared as described below in phosphate buffered saline with bovine serum albumin, EDTA, dye, and 0.1% sodium azide, and stored at 4° C.

Rabbit Anti-Ferritin/Anti-TSH Solution

Rabbit anti-ferritin serum and purified rabbit anti-TSH antibody were diluted in a phosphate buffered saline with bovine serum albumin, EDTA, dye, and 0.1% sodium azide, and stored at 4° C.

Precipitating Solution

Goat anti-rabbit immune serum was diluted in phosphate buffered saline with polyethylene glycol and 0.1% sodium azide, and stored at 4° C.

Zero Standard

Contained a protein base with phosphate buffer, sodium chloride, and 0.1% sodium azide, and was stored at 4° C.

Ferritin/TSH Standards

Five concentrations, each containing human liver ferritin and human TSH in a protein base with phosphate buffer, sodium chloride, and 0.1% sodium azide. The concentrations were (ferritin/TSH) 10/5, 25/10, 100/50, 400/100 and 800/100 ng/μml. Stored at 4° C.

Preparation of $^{125}$I Ferritin/$^{57}$Co Anti-TSH Tracer Solution

One milligram of lyophilized affinity purified goat anti-TSH was mixed dry with 0.3 milligrams of diethylenetriaminepentaacetic anhydride (DTPA). 100 μl of metal-free 0.1 M HEPES, pH 7.0, was added dropwise. The reaction mixture was allowed to incubate for 15 minutes at room temperature. The resulting preparation was passed through a Sephadex G-75 (1×20 cm) column, equilibrated and eluted with metal-free 0.5 M acetate buffer, pH 5.8. Fractions (1 ml) were collected and the presence of anti-TSH-DTPA identified by absorbance at 280 nm. The peak fraction was diluted with 0.5 M acetate buffer to contain 40 μg of anti-TSH-DTPA per 200 μl, aliquoted into vials (200 μl vial) and lyophilized.

One vial containing 40 μg of lyophilized anti-TSH-DTPA was reconstituted with 200 μl of deionized water. To the resulting solution, 1 mCi (6 μl) of carrier free $^{57}$CoCl$_2$/μg was added and allowed to react for one hour at room temperature. The reaction mixture was passed through a Sephadex G-75 column, equilibrated and eluted with metal-free 0.01 M phosphate-buffered saline (PBS) containing 5% (V/V) normal rabbit serum, 0.1% (W/V) bovine serum albumin and a red dye, Congo Red. The fractions (1 ml) were collected and monitored for radioactivity with a gamma counter. A peak containing $^{57}$Co-DTPA-anti-TSH was eluted near the void volume with an estimated specific activity of 8 μCi of $^{57}$Co/μg of anti-TSH. Seventy-five μl of the peak $^{57}$Co-DTPA-anti-TSH (about 10 μCi) were added to 10 ml of $^{125}$I labeled ferritin in phosphate-buffered saline containing 0.5% bovine albumin, 0.05 M EDTA, 0.1% (W/V) sodium azide and red dye.

ASSAY PROCEDURE

1. The assay tubes were labeled according to the following general outline:

| Assay Tube | Contents |
|---|---|
| 1, 2 | Total Counts |
| 3, 4 | Standard: 0 ng/ml Ferritin<br>0 μIU/ml TSH |
| 5, 6 | Standard: 10 ng/ml Ferritin<br>5 μIU/ml TSH |
| 7, 8 | Standard: 25 ng/ml Ferriti<br>10 μIU/ml TSH |
| 9, 10 | Standard: 100 ng/ml Ferritin<br>50 μIU/ml TSH |
| 11, 12 | Standard: 400 ng/ml Ferritin<br>100 μIU/ml TSH |
| 13, 14 | Standard: 800 ng/ml Ferritin<br>400 μIU/ml TSH |
| 15–100 | Patient Samples |

2. 200 Microliter portions of the zero standard, ferritin/TSH standards or patient samples were accurately pipetted into appropriately labeled assay tubes.

3. 100 Microliter portions of $^{125}$I Ferritin/$^{57}$Co Anti-TSH Tracer were accurately pipetted into all tubes.

4. 100 Microliter portions of Rabbit Anti-Ferritin-/Anti-TSH Solution were accurately pipetted into all tubes except total count, and vortexed.

5. Incubation was carried out at room temperature for 60 minutes.

6. The precipitating solution was shaken immediately before use, 1.0 ml was pipetted into all tubes except total count tubes and vortexed thoroughly.

7. Incubation was carried out for 15 minutes at room temperature.

8. The tubes were centrifuged for 15 minutes at a relative centrifugal force (RCF) of 1500×g.

9. All but the total count tubes were decanted and the supernatant discarded, taking care not to disturb the pellet. The lip of the test tube was blotted with absorbant material to remove residual drops.

10. The tubes were counter on a gamma counter set respectively for $^{125}$I and $^{57}$Co.

CALCULATION OF RESULTS

1. The counts per minute (cpm) were averaged for all duplicate tubes. Correction was made for background.

2. "Normalized" binding for $^{57}$Co cpm's was calculated by the following equation:

$$\text{Normalized \% } ^{57}\text{Co Bound}(N^{57}\text{Co \% B}) = \frac{(\text{Average } ^{57}\text{Co CPM}) - (\text{Average } ^{57}\text{Co of 0 Std}) \times 100}{(2 \times \text{avg. } ^{57}\text{Co CPM of 200}\mu \text{ IU/ml Std}) - (2 \times \text{avg. } ^{57}\text{Co CPM of 0 Std})}$$

3. The % $^{125}$I Bound ($^{125}$IB/Bo) was calculated by the following equation:

Percent $^{125}$I Binding ($^{125}$IB/Bo) =

$$\frac{\text{Avg. } ^{125}\text{I CPM of Standard of Sample}}{\text{Avg. } ^{125}\text{I CPM of 0 Std.}} \times 100$$

4. N$^{57}$Co % B and $^{125}$IB/Bo for the standards were plotted on logit/log graph paper using the ordinate (Y axis) for N$^{57}$Co % B or $^{125}$IB/Bo and the abscissa (X axis) for the stated concentration of the standard. The TSH concentrations were used to plot versus the N $^{57}$Co % B values, while the ferritin concentrations were used to plot versus $^{125}$IB/Bo.

5. A "Best fit" straight line was drawn through the TSH standard vs. N$^{57}$Co % B points on the graph and another straight line was drawn through the ferritin standard vs. $^{125}$IB/Bo points. TSH and ferritin values for the samples were interpolated from the appropriate standard curve.

TYPICAL DATA

| | TSH I($^{57}$Co) | | | |
|---|---|---|---|---|
| Tube contents | Average CPM | N%B | Average CPM | B/Bo |
| Total Count | 309461 | — | 74936 | — |
| 0/0 Standard | 19770 | 7.6 | 32442 | 100 |
| 10/5 Standard | 33131 | 10.4 | 28411 | 87.6 |
| 25/10 Standard | 38073 | 18.7 | 24019 | 74.0 |
| 100/50 Standard | 68103 | 27.3 | 16691 | 51.5 |
| 400/100 Standard | 90333 | 39.9 | 9986 | 30.8 |
| 800/200 Standard | 108214 | 50.0 | 8781 | 27.1 |

The above discussion of this invention is directed primarily to preferred embodiments and practices thereof. It will be readily apparent to those skilled in the art that further changes and modifications in the actual implementation of the concepts described herein can easily be made without departing from the spirit and scope of the invention as defined by the following claims.

I claim:

1. A method of multiple simultaneous assay involving at least two radiolabeled materials for detection or determination of the analytes being assayed, each of said radiolabeled materials being present for the detection or determination of a separate analyte, wherein at least one portion of the assay is an immunoradiometric assay and the remaining portion(s) of the assay, if any, is/are another radioassay technique comprising treating a sample containing analytes to be detected with a composition containing at least two radiolabeled materials for detection or determination of the analytes being assayed, each of said radiolabeled materials being present for the detection or determination of a separate analyte, at least one of said radiolabeled materials being a stable coordination compound of the formula:

metal isotope-chelator-antibody to analyte and wherein, when more than one of said coordination compounds is present for use in multiple simultaneous immunoradiometric assays, each stable coordination compound has a different metal isotope and an antibody to a different analyte and detecting or determining each analyte in the sample.

2. A multiple simultaneous assay as recited in claim 1 in which a composition comprising more than one of said stable coordination compounds is employed.

3. A multiple simultaneous assay as recited in claim 1 in which radiolabeled antigen for use in a competitive radioimmunoassay is also employed.

4. A multiple simultaneous assay as recited in claim 1 in which the chelator portion of at least one of said coordination compounds is 1-(p-bromoacetamidobenzyl)ethylenediaminetetraacetic acid.

5. A multiple simultaneous assay as recited in claim 1 in which the chelator portion of at least one of said coordination compounds is hydroxyethylethylenediaminetetraacetic acid.

6. A multiple simultaneous assay as recited in claim 1 in which the chelator portion of at least one of said coordination compounds is a polyamino-polycarboxylate of the general formula:

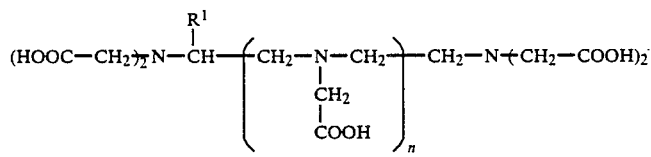

wherein $R^1$ is hydrogen, phenyl or $NO_2-$, $NH_2-$ or $SO_3H$-substituted phenyl and n is an integer of 0 or 1.

7. A multiple simultaneous assay as recited in claim 6 in which said polyaminopolycarboxylate is ethyelendiaminetetraacetic acid.

8. A multiple simultaneous assay as recited in claim 6 in which said polyaminopolycarboxylate is diethylenetriaminepentaacetic acid.

9. A multiple simultaneous assay as recited in claim 6 in which said polyaminopolycarboxylate is ethylenedinitrilotetraacetic acid.

10. A multiple simultaneous assay as recited in claim 1 in which said composition contains a coordination compound having the formula:

$^{57}$Co—chelator—monoclonal antibody to thyrotropin.

11. A multiple simultaneous assay as recited in claim 1 in which said composition contains a coordination compound having the formula:

$^{57}$Co—chelator—rabbit anti-TSH.

12. A multiple simultaneous assay as recited in claim 1 in which said composition contains a coordination compound having the formula:

$^{57}$Co—chelator—goat anti-TSH.

13. A multiple simultaneous assay as recited in any one of claims 1-9 in which said composition is substantially free of metal contaminants.

14. A multiple simultaneous assay as recited in any one of claims 1-9 in which the antibody to analyte portion of at least one of said coordination compounds is a monoclonal antibody.

15. A multiple simultaneous assay as recited in any one of claims 1-9 in which the antibody to analyte portion of at least one of said coordination compounds is a monoclonal antibody.

16. A multiple simultaneous assay as recited in any one of claims 2 and 1 in which the metal isotope portion of at least one of said coordination compounds is selected from the group consisting of isotopes of cobalt, iron, indium, technetium, europium and terbium.

17. A multiple simultaneous assay as recited in claim 16 in which said isotope is an isotope of cobalt.

18. A multiple simultaneous assay as recited in claim 17 in which said isotope of cobalt is $^{57}$Co.

19. A multiple simultaneous assay as recited in claim 16 in which said isotope is an isotope of iron.

20. A multiple simultaneous assay as recited in claim 19 in which said isotope of iron is $^{59}$Fe.

21. A multiple simultaneous assay as recited in any one of claims 10-12 in which the chelator portion of said coordination compound is ethyelendiaminetetraacetic acid.

22. A multiple simultaneous assay as recited in any one of claims 10-12 in which the chelator portion of said coordination compound is diethylenetriaminepentaacetic acid.

* * * * *